(12) United States Patent
Ihn et al.

(10) Patent No.: US 10,514,363 B2
(45) Date of Patent: Dec. 24, 2019

(54) LASER ULTRASOUND SCANNING FOR VISUALIZING DAMAGE OR IRREGULARITIES

(71) Applicant: The Boeing Company, Chicago, IL (US)

(72) Inventors: Jeong-Beom Ihn, Bellevue, WA (US); Gary E. Georgeson, Tacoma, WA (US); William Paul Motzer, Mount Pleasant, SC (US)

(73) Assignee: The Boeing Company, Chicago, IL (US)

( * ) Notice: Subject to any disclaimer, the term of this patent is extended or adjusted under 35 U.S.C. 154(b) by 135 days.

(21) Appl. No.: 15/904,114

(22) Filed: Feb. 23, 2018

(65) Prior Publication Data
US 2019/0265200 A1  Aug. 29, 2019

(51) Int. Cl.
*G01N 29/04* (2006.01)
*G01N 29/26* (2006.01)
*G01N 29/24* (2006.01)

(52) U.S. Cl.
CPC ....... *G01N 29/2418* (2013.01); *G01N 29/041* (2013.01); *G01N 29/043* (2013.01);
(Continued)

(58) Field of Classification Search
CPC ............. G01N 29/2418; G01N 29/043; G01N 29/262; G01N 29/041; G01N 2291/0289; G01N 2291/0231
(Continued)

(56) References Cited

U.S. PATENT DOCUMENTS 8,965,100 B2   2/2015  Lin et al.
9,164,066 B1  10/2015  Bossi et al.
(Continued)

FOREIGN PATENT DOCUMENTS

WO   WO 2018/002871   1/2018

OTHER PUBLICATIONS

Park et al., *Visualization of hidden delamination and debonding in composites through noncontact laser ultrasonic scanning*, Composites Science and Technology 100, pp. 10-18, 2014.
(Continued)

*Primary Examiner* — Jacques M Saint Surin
(74) *Attorney, Agent, or Firm* — DASCENZO Intellectual Property Law, P.C.

(57) ABSTRACT

Methods and systems may be configured to integrate data from fixed nondestructive inspection sensors positioned on a test specimen and data from laser ultrasound scans of the test specimen, in order to monitor and track damage and stress indications in the test specimen in real-time during mechanical stress testing of the test specimen. Data from the laser ultrasound scans may identify emergent areas of interest within the test specimen that were not predicted by stress analysis, and further allow for reconfiguration of the test plan in view of the emergent areas of interest, without having the stop the test. Laser ultrasound scans may be performed on the entire test specimen, with high-resolution scans being performed on emergent areas of interest. Thus, stress indications, or stress effects, in the test specimen may be measured, identified, and tracked in real-time (e.g., as growth is propagating) in a test specimen undergoing structural tests.

20 Claims, 6 Drawing Sheets

(52) U.S. Cl.
CPC ... *G01N 29/262* (2013.01); *G01N 2291/0231* (2013.01); *G01N 2291/0289* (2013.01)

(58) Field of Classification Search
USPC .......................................................... 73/577
See application file for complete search history.

(56) References Cited

U.S. PATENT DOCUMENTS

| | | | |
|---|---|---|---|
| 9,358,331 B2* | 6/2016 | Fulkerson | A61M 1/3641 |
| 9,383,342 B1 | 7/2016 | Bossi et al. | |
| 9,404,898 B1 | 8/2016 | Georgeson et al. | |
| 9,414,026 B2 | 8/2016 | Blanchard et al. | |
| 9,433,720 B2* | 9/2016 | Updyke | A61M 1/284 |
| 9,746,445 B2 | 8/2017 | Hafenrichter et al. | |
| 9,861,733 B2* | 1/2018 | Burbank | A61M 1/285 |
| 9,907,897 B2* | 3/2018 | Burbank | A61M 1/1656 |
| 10,035,103 B2* | 7/2018 | Fulkerson | A61M 1/14 |
| 2002/0052055 A1* | 5/2002 | Nikawa | G01R 31/311 |
| | | | 438/16 |
| 2008/0291465 A1 | 11/2008 | Lorraine et al. | |

OTHER PUBLICATIONS

Liu et al., *Survey: State of the Art in NDE Data Fusion Techniques*, IEEE Transactions on Instrumentation and Measurement, vol. 56, No. 6, Dec. 2007.
European Patent Office, Extended European Search Report for related European Application No. 19158142, dated Jun. 26, 2019.

* cited by examiner

LASER ULTRASOUND SCANNING FOR VISUALIZING DAMAGE OR IRREGULARITIES

FIELD

The present disclosure relates to methods and devices for testing and/or inspecting a test specimen using laser ultrasound scanning and fixed nondestructive inspection sensors for visualizing and/or monitoring stress effects, damage, and/or irregularities in the test specimen.

BACKGROUND

Composite structures are often structurally tested during design and/or manufacture of the composite structure, as well as once the composite structure is in use. For example, a mechanical apparatus may be used to bend the composite structure, periodically flex the composite structure, and/or limit load the composite structure in order to mechanically test the composite structure. In some cases, this may be performed during design and manufacture of a composite structure, such as to analyze fatigue fault initiation and growth within the composite structure.

Fixed non-destructive inspection (NDI) sensors may be attached to test piece, or test specimen, (e.g., a composite structure being tested) to detect any indications of stress or damage during the testing. Often, single point ultrasonic transducers are mounted on the test specimen in locations where finite element analysis indicates they will be most useful. However, these fixed sensors tend to only collect data in the areas under the sensors and thus cannot monitor the entire composite structure. If indications appear in unexpected locations, data density in those unexpected locations may be sparse or non-existent. If unexpected indications occur, technicians may be required to stop the test and reposition the fixed sensors in order to obtain data from different locations on the structure. Oftentimes this may result in invalidating the entire test (and therefore having to restart it from the beginning), if, for example, the fixed sensors cannot be safely removed and repositioned without relieving the test stress placed on the composite structure.

Current non-contact testing methods, such as optical, IR thermography, and digital image correlation, are limited by their depth of penetration and often cannot provide adequate information. Other methods, such as microwave- and radar-based testing methods, often are limited by their low-resolution capabilities. Some X-ray-based testing methods may provide high resolution but are not well-suited for composite structures, especially large composite parts. Additionally, these conventional testing systems tend to be large and difficult to move.

Laser ultrasonic non-destructive inspection systems are also utilized to verify the structural integrity of composite materials. In this process, a pulsed generation laser is directed at the surface of the test specimen, with the beam being absorbed into a shallow volume of the material (e.g., the top 10-100 microns of the test specimen). The rapid absorption of the pulse laser energy creates a localized heating, which results in expansion of the material (referred to as thermo-elastic expansion), inducing a stress wave. These waves interrogate a feature of interest in the interior or surface of the test specimen, and then propagate to the surface position of a detection laser beam. The resulting surface displacement is measured with a laser ultrasonic receiver. The measured signal is then processed to yield and display the desired information. However, these conventional laser inspection systems have limited capability for real-time structural integrity monitoring and damage characterization, which may be due to limited resolution, needing a direct line of sight to the test piece, and/or having a limited thickness through which the laser inspection systems may be useful for scanning.

SUMMARY

Presently disclosed systems and methods may be configured for measuring, identifying, and tracking damage indications in structures during structural tests, in real-time (e.g., as growth is propagating). Such systems and methods may utilize (e.g., integrate) data from one or more nondestructive inspection (NDI) sensors mounted on the structure, as well as from laser ultrasound scans performed by a laser ultrasound device (which may be non-contact with respect to the structure). In some systems, structures may be inspected with access to only a single side of the structure. Such systems and methods may be used, for example, to compare in-service (assembled) parts with the as-built record taken during original manufacturing process.

Disclosed methods of testing a test specimen (e.g., a composite structure) may include monitoring the test specimen with an NDI sensor fixed with respect to the test specimen, scanning at least a portion of the test specimen using a laser ultrasound device, storing the first laser ultrasound scan, and mechanically testing the test specimen. A plurality of subsequent respective laser ultrasound scans of stress effects within the test specimen may be performed during the mechanically testing the test specimen, and each subsequent respective laser ultrasound scan of the test specimen may be stored in order to compare each subsequent respective laser ultrasound scan of the test specimen with a previous respective laser ultrasound scan of the test specimen. In disclosed methods, the fixed NDI sensor may be configured to monitor indications of damage in or on the test specimen, and the fixed NDI sensor may further be configured to produce fixed sensor data related to the test specimen. Each time the laser ultrasound device scans the composite structure, a laser ultrasound scan of stress effects within the test specimen is produced, and data from such scans may be integrated with fixed sensor data from the fixed NDI sensors to monitor and/or characterize damage in the composite structure. While the fixed NDI sensors are generally positioned on the surface of the composite structure, the laser ultrasound device is generally spaced apart from the composite structure (e.g., non-contact). Disclosed methods may allow for reconfiguration of the test plan for the composite structure during the mechanical testing, to accommodate emergent indications of damage or stress detected by disclosed systems and methods in areas not predicted by stress analysis.

Disclosed systems for testing a test specimen may include the test specimen, a laser ultrasound device located apart from the test specimen, a plurality of fixed NDI sensors fixed with respect to the test specimen (e.g., spaced apart from each other on a surface of the test specimen), and a processor. The laser ultrasound device may be configured to generate and direct a laser beam at the test specimen, thereby producing a plurality of ultrasonic waves within the test specimen, and may be further configured to produce a detection laser beam and measure an alteration in the detection laser beam as a result of the plurality of ultrasonic waves. The laser ultrasound device may be further configured to scan at least a portion of the test specimen and produce a respective laser ultrasound scan of stress effects within the test specimen periodically during mechanical testing of the test specimen. Each respective fixed NDI sensor may be configured to produce fixed sensor data related to a respective location of the test specimen corresponding to the location of the respective fixed NDI sensor. The processor may be configured to integrate data from the plurality of fixed NDI sensors and from the respective laser ultrasound scans produced by the laser ultrasound device, to monitor or inspect the test specimen during mechanical testing of the test specimen.

DESCRIPTION

Figure 1:
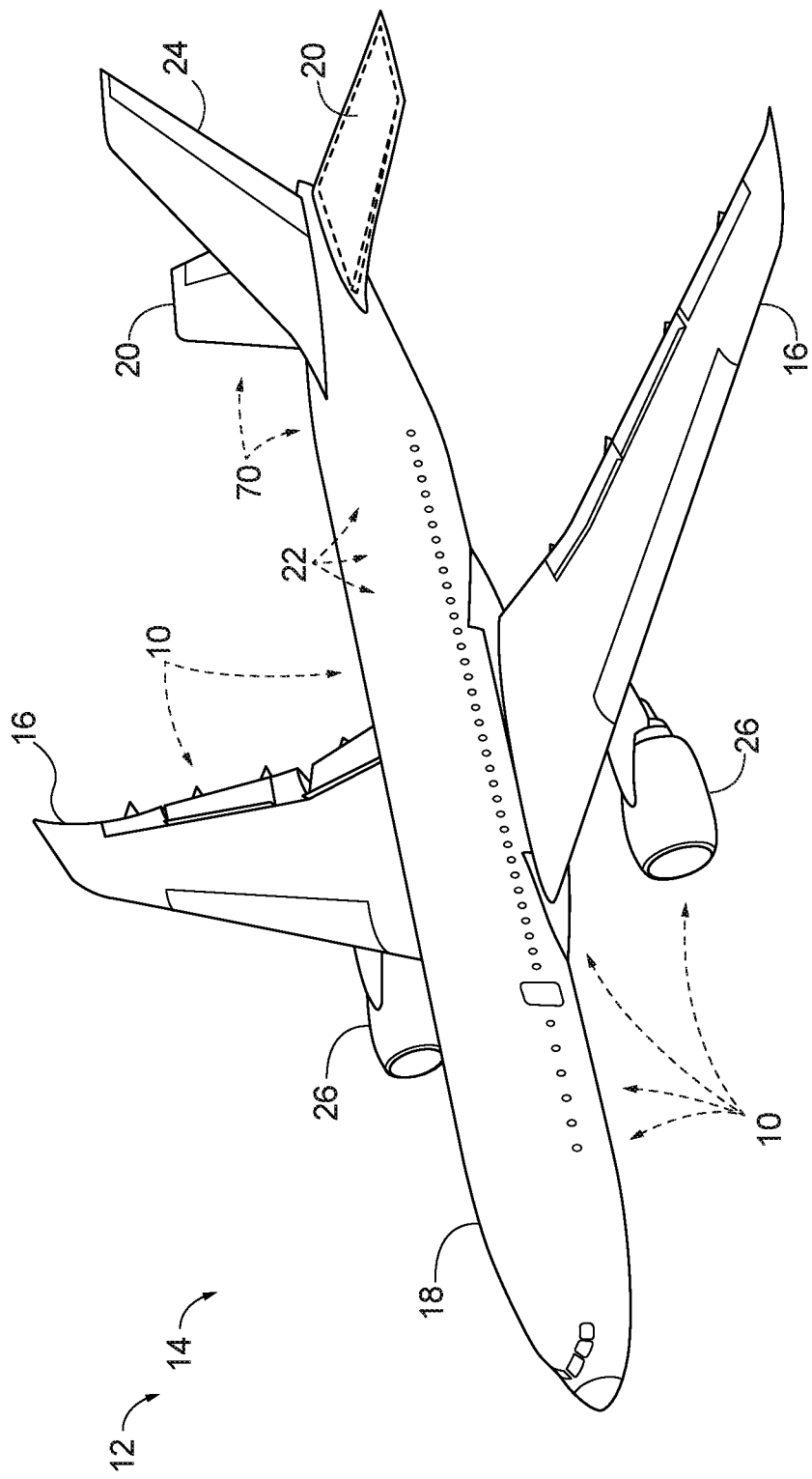
FIG. 1 is a schematic illustration of an example of an aircraft comprising one or more composite parts.

With reference to FIG. 1, one or more composite structures 10 may be included in an apparatus 12. Composite structures 10 may be utilized in many different industries and applications, such as aerospace, automotive, electronic, construction, military, recreation, and/or motorsport industries. In FIG. 1, an example of apparatus 12 that may include one or more composite structures 10 generally is illustrated in the form of an aircraft 14. Aircraft 14 may take any suitable form, including commercial aircraft, military aircraft, or any other suitable aircraft. While FIG. 1 illustrates an aircraft 14 in the form of a fixed wing aircraft, other types and configurations of aircraft are within the scope of aircraft 14 according to the present disclosure, including (but not limited to) rotorcraft and helicopters.

Apparatus 12 (e.g., aircraft 14) may include one or more composite structures 10. As illustrative, non-exclusive examples, composite structures 10 may be utilized in such aircraft structures as wings 16, fuselages 18, horizontal stabilizers 20, overhead storage bins 22, vertical stabilizers 24, and engine housings 26; however, other components of aircraft 14 additionally or alternatively may include composite structures 10. Other applications in aircraft 14 for composite structures 10 include floor panels, interior walls, food handling galley assemblies, wing control surfaces, passenger storage racks, thrust deflector assemblies, capsule panels, ablative shields for nose cones, instrumentation enclosures and shelves, and bulkhead panels. In other industries, examples of apparatus 12 (including one or more composite structures 10) may include or be a portion of space satellites, electronic radome construction, transit vehicles, shipping containers, shelters, large antennae or disk reflectors, refrigeration panels, rapid transit floor panels, shipboard electronic deck shelters, cargo pallets, automobile bodies, architectural curtain walls, partitions, divider panels, expandable hospital shelters, and/or interior structures of an assembly.

Figure 2:
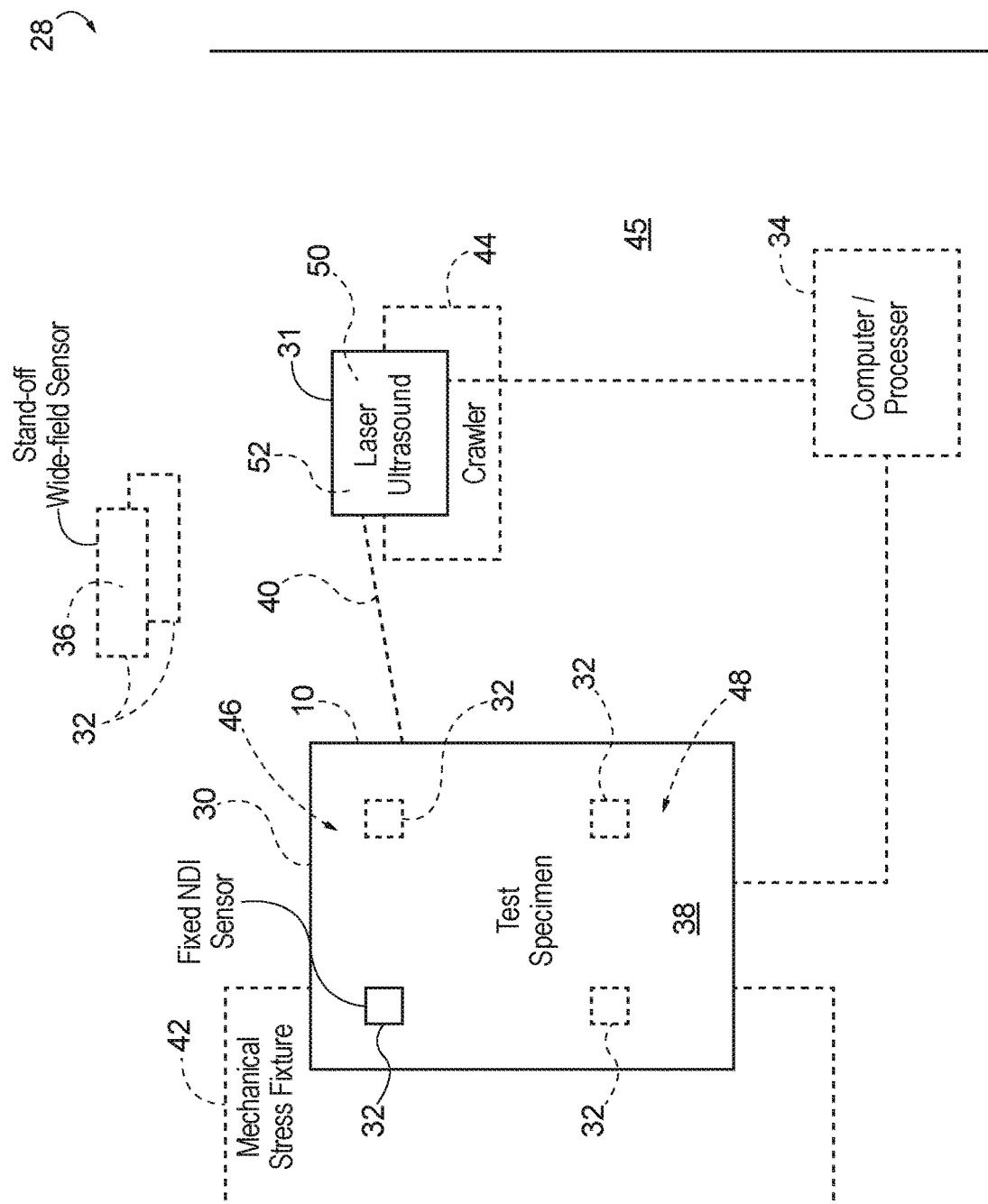
FIG. 2 is a schematic representation of illustrative examples of systems for testing a composite structure, according to the present disclosure.

FIG. 2 schematically illustrates systems 28 for testing a test specimen 30, such as composite structure 10, according to the present disclosure. For example, test specimen 30 may be a composite structure 10 intended for use in apparatus 12 (e.g., composite structure 10 may be an example of test specimen 30). Test specimen 30 may be tested according to the present disclosure during the design phase, during the manufacturing phase, and/or during the in-service phase of use. Generally, in the figures, elements that are likely to be included in a given example are illustrated in solid lines, while elements that are optional to a given example are illustrated in broken lines. However, elements that are illustrated in solid lines are not essential to all examples of the present disclosure, and an element shown in solid lines may be omitted from a given example without departing from the scope of the present disclosure.

Systems 28 generally include test specimen 30, one or more non-destructive inspection (NDI) sensors 32, a laser ultrasound device 31 (which may be located apart from test specimen 30), and a processor 34 configured to receive, monitor, integrate, process, and/or analyze data from laser ultrasound device 31 and NDI sensors 32. Processor 34 also may be referred to herein as a control unit 34. NDI sensors 32 are fixed with respect to test specimen 30. For example, one or more NDI sensors 32 may be mounted on, coupled to, fixed to, or secured to test specimen 30 via any suitable fasteners, adhesives, and/or other coupling. Additionally or alternatively, one or more NDI sensors 32 may be fixed at a location spaced apart from test specimen 30 (e.g., one or more of NDI sensors 32 may be a stand-off wide-field sensor 36). NDI sensors 32 are configured to monitor or detect indications of damage in or on test specimen 30, and produce corresponding fixed sensor data related to test specimen 30. NDI sensors 32 are generally spaced apart from one another in various locations on a surface 38 of test specimen 30. In some examples, NDI sensors 32 may be positioned on multiple different surfaces 38 of test specimen 30. In some examples, NDI sensors 32 are positioned in areas of test specimen 30 that are expected to experience the greatest stresses and/or damage during testing and/or use, such as those locations predicated by finite element analysis.

Laser ultrasound device 31 is configured to generate and direct a laser beam 40 (e.g., a pulsed laser beam 40) at test specimen 30, thereby producing a plurality of ultrasonic waves within test specimen 30. Laser ultrasound device 31 is further configured to produce a detection laser beam and measure an alteration in the detection laser beam as a result of the plurality of ultrasonic waves produced in test specimen 30 by laser beam 40. Laser ultrasound device 31 is further configured to scan at least a portion of test specimen 30 and produce a spatial laser ultrasound scan of damage and/or stress effects within test specimen 30 resulting from stresses applied to test specimen 30.

Laser ultrasound device 31 may be positioned at a location away from test specimen 30, such as at least 0.5 meters (m) away, at least 1 m away, at least 2 m away, at least 3 m away, and/or at least 5 m away from test specimen 30. Additionally or alternatively, laser ultrasound device 31 may be positioned outside of a portion of test specimen 30 being tested. For example, if a first portion 46 of testing specimen 30 is being tested by system 28, then laser ultrasound device 31 may be positioned within a second portion 48 of test specimen 30, or may be positioned spaced apart from test specimen 30. In other examples, laser ultrasound device 31 may be positioned within the same portion of test specimen 30 being tested. In some systems 28, laser ultrasound device 31 includes an alignment system 50 configured to align and project laser beam 40 to the desired location on test specimen 30. Additionally or alternatively, laser ultrasound device 31 may include a detection system 52 configured to detect the alterations in the detection laser beam as a result of the ultrasonic waves produced in the test specimen.

In some systems 28, test specimen 30 is subjected to mechanical testing and/or inspection. For example, test specimen 30 may be mechanically tested (e.g., loaded or stressed) via a mechanical stress fixture 42. Mechanical stress fixture 42 is configured to support and position test specimen 30 for testing, in some systems 28. For example, mechanical stress fixture 42 may be configured to maintain some or all of test specimen 30 in a particular position and/or orientation. In some examples, mechanical stress fixture 42 is configured to perform a bent wing test of a wing for an aircraft, periodically flex test specimen 30, subject test specimen 30 to one or more fatigue cycles, bend test specimen 30 to its limit load, statically load test specimen 30, apply an external load to test specimen 30, pressurize test specimen 30, internally interrogate test specimen 30, position test specimen 30 during mechanical testing, and/or move test specimen 30 during mechanical testing of test specimen 30. Some testing methods risk causing structural failure of test specimen 30. Use of laser ultrasound device 31 may be advantageous in such cases, as the laser ultrasound scan is a non-contact scan (meaning that physical contact with test specimen 30 is generally not required), and thus there may be less risk of damage to laser ultrasound device 31 in cases of structural failure of test specimen 30. Additionally, operators or technicians performing the testing on test specimen may remain safely at a distance from a stressed test specimen 30.

In use, NDI sensors 32 are monitored, and test specimen 30 is scanned using laser ultrasound device 31. Generally, substantially the entire surface 38 of test specimen 30 is scanned at or before the beginning of the testing, though in other examples, only a portion of surface 38 of test specimen 30 may be scanned at or before beginning the testing. Each time some or all of surface 38 of test specimen 30 is scanned by laser ultrasound device 31, a respective laser ultrasound scan of stress effects within test specimen 30 is produced. The laser ultrasound scans spatially map stress effects, pre-existing conditions, manufacturing defects, and/or damage with respect to surface 38 of test specimen 30.

Stress effects may include any stress effects and/or damage to test specimen 30, such as delaminations, voids (e.g., subsurface voids), disbonds, cracks, micro-cracks, surface damage, impact-induced damage, moisture, corrosion, fatigue fault, and/or skewed defects in test specimen 30. The laser ultrasound scans may be configured to provide additional information regarding test specimen 30 as well, such as thickness measurements, materials characterization, and/ or fatigue fault initiation/growth.

During mechanical testing, laser ultrasound device 31 performs a plurality of scans of test specimen 30, which may be scans of at least substantially the entire surface 38 of test specimen 30, and/or may be scans of a portion of surface 38 of test specimen 30. In some examples, measures may be taken to scan as much of surface 38 of test specimen 30 as possible. For example, guided waves may be used to guide, or "steer," wave propagation around areas where NDI sensors 32 may be fixed, and/or to areas of interest within test specimen. Such guided waves may be transmitted by, for example, stand-off transducers that are positioned so as to not interfere with laser beams transmitted towards surface 38 from laser ultrasound device 31. Additionally or alternatively, NDI sensors 32 may be positioned on surface 38, to the extent possible, so as to not obscure a line of sight between laser ultrasound device 31 and surface 38. For example, NDI sensors 32 may be positioned on a peripheral region of test specimen 30, and/or on a far side, or back side of test specimen 30 from surface 38 being scanned by laser ultrasound device 31. Additionally or alternatively, laser ultrasound device 31 may be configured to generate or produce guided or structural waves that can be directed at an area of surface 38 on a first side of a respective NDI sensor 32, and then pick up the resulting signal within an area of surface 38 on a second side of the respective NDI sensor 32. Additionally or alternatively, if a respective NDI sensor 32 obscures laser ultrasound scan data for a particular area of surface 38, data from the respective NDI sensor 32 may be used to provide information on that area of surface 38, such that the data may be merged to effectively complete the laser ultrasound scan for that area of surface 38.

In some examples, laser ultrasound device 31 performs periodic scans of some or all of test specimen 30 during testing. In some examples, and as will be explained in more detail below, laser ultrasound device 31 performs scans of targeted areas of test specimen 30, corresponding to areas of interest indicated by data from fixed NDI sensors 32 and/or indicated by data from changes detected in earlier scans. Each laser ultrasound scan is stored (e.g., by control unit 34), such that a respective laser ultrasound scan can be compared with a previous or earlier respective laser ultrasound scan, to monitor changes in test specimen 30.

Systems 28 are configured to integrate fixed sensor data from NDI sensors 32 with data from one or more laser ultrasound scans. Systems 28 thereby may be used for, for example, mechanical testing (e.g., sub-scale or full-scale mechanical testing) of test specimen 30, for analysis validation of test specimen 30, for inspection of test specimen 30, and/or for in-service inspection of test specimen 30 (e.g., to compare in-service (assembled) parts with the as-built record taken during original manufacturing process). The use of laser ultrasound device 31 in combination with NDI sensors 32 as described herein may be advantageously configured to efficiently monitor large test specimens 30 and/or optimized areas of test specimen 30.

Some systems 28 include a crawler system 44 configured to automate the performance of a plurality of laser ultrasound scans of test specimen 30 by laser ultrasound device 31. For example, laser ultrasound device 31 may be housed in, supported by, and/or mounted on crawler system 44, which may be a mobile system configured to move and position laser ultrasound device 31 with respect to test specimen 30. Crawler system 44 may thus be configured to position laser ultrasound device 31 in a plurality of different locations in order to perform a laser ultrasound scan of a plurality of different locations or portions of test specimen 30. For example, crawler system 44 may position laser ultrasound device 31 in a first location within a testing environment 45 to perform a laser ultrasound scan of a first portion 46 of test specimen 30, and then crawler system 44 may move laser ultrasound device 31 to a second location within testing environment 45 to perform a laser ultrasound scan of a second portion 48 of test specimen 30. Additionally or alternatively, crawler system 44 may be configured to move on a surface (e.g., surface 38) of test specimen 30. In other examples, laser ultrasound device 31 may be mounted on, coupled to, supported by, and/or housed in a different mobile platform (e.g., a cart or a vehicle, such as a truck or a boat) or in a stationary structure, such as a system tower, a gantry, or a tripod.

Test specimen 30 may be any suitable test specimen. In some examples, test specimen 30 may be a composite structure intended for use in or currently in use in an aircraft (e.g., composite structure 10 of aircraft 14 of FIG. 1). In some examples, test specimen 30 is a composite structure with complex three-dimensional contours. In some examples, test specimen 30 is a large structure (e.g., a large fuselage section of an aircraft) and/or may include areas with tight radii that are difficult to access. For example, test specimen 30 may be a fuselage stringer for an aircraft. In some examples, test specimen 30 may be a hazardous and/or inaccessible or difficult-to-access component or structure. Test specimen 30 may be a specimen being developed (e.g., in the design stage), such that mechanical testing is evaluating the design of the test specimen. In other examples, test specimen 30 may be a specimen being manufactured, such that mechanical testing is inspecting and/or certifying the part during or after manufacture. In other examples, test specimen 30 may be a specimen that is currently in-service, such that mechanical testing is inspecting for damage that may need to be repaired or that may warrant removal and replacement of the in-service part. Test specimen 30 may be a sub-scale composite structure, a mid-scale composite structure, and/or a full-scale composite structure. In some examples, test specimen 30 may be formed of metallic materials and/or other materials.

NDI sensors 32 may be any suitable NDI sensor that can provide information about the performance or state of test specimen 30, while subjecting test specimen 30 to little or no damage. In some systems 28, at least one of NDI sensors 32 may be an acoustic emission sensor, a PZT transducer, an NDI sensor, an ultrasonic transducer, a bonded PZT sensor, a fiber optic sensor, a stand-off thermography system, a stress gauge, an onboard sensor for an in-service part, and/or a strain gauge. Systems 28 generally include a plurality of NDI sensors 32, though in some examples, a single NDI sensor 32 may be used. Systems 28 may include a plurality of different types of NDI sensors 32, or may include just one type of NDI sensor 32. In some examples, system 28 includes NDI sensors 32 in the form of ultrasonic transducers that produce different types of waves in test specimen 30. For example, systems 28 may include one or more NDI sensors 32 that produce A-scans, one or more NDI sensors 32 that produce plate waves, and/or one or more NDI sensors 32 that produce surface waves in test specimen 30. Additionally or alternatively, systems 28 may include one or more NDI sensors 32 configured to generate interface waves (e.g., Stoneley waves) that are configured to interrogate bondlines of test specimen 30, one or more NDI sensors 32 configured to generate surface waves (e.g., Rayleigh waves) that are configured to interrogate micro-cracking and/or surface damage to test specimen 30, one or more NDI sensors 32 configured to generate lamb waves that are configured to interrogate impact-induced delamination, disbonds, and/or cracks in test specimen 30, and/or one or more NDI sensors 32 configured to generate shear vertical waves that are configured to interrogate skewed defects in test specimen 30.

Figure 3:
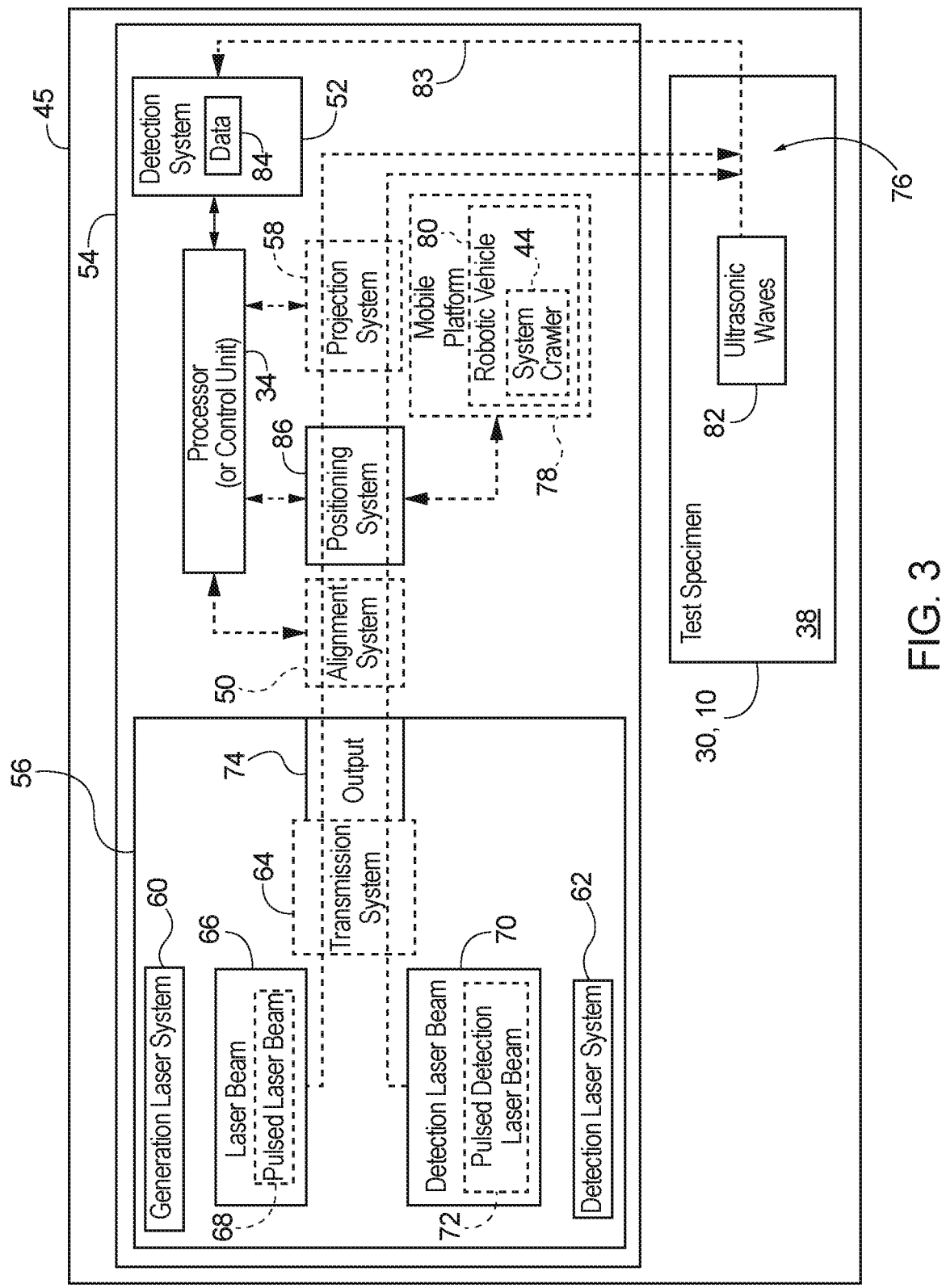
FIG. 3 is a block diagram of a testing environment including systems for testing a composite structure according to the present disclosure.

FIG. 3 illustrates a block diagram of an example of testing environment 45 in which a laser ultrasound device 54 (which is an example of laser ultrasound device 31) may be used to inspect test specimen 30, or a region or portion thereof. As depicted, laser ultrasound device 54 includes a laser system 56, a projection system 58, and detection system 52. Laser system 56 may include a generation laser system 60, a detection laser system 62, and, in some cases, a transmission system 64.

In use, generation laser system 60 of laser system 56 generates a laser beam 66 (which is an example of laser beam 40). Laser beam 66 may take the form of, for example, a pulsed laser beam 68. Pulsed laser beam 68 is formed by pulses of laser energy. In other words, pulsed laser beam 68 is formed by pulses of light that are emitted in the form of a beam. Similarly, detection laser system 62 generates a detection laser beam 70. Detection laser beam 70 may take the form of, for example, a pulsed detection laser beam 72.

In one illustrative example, generation laser system 60 and detection laser system 62 may be implemented using a carbon dioxide ($CO_2$) laser system. In another illustrative example, generation laser system 60 and detection laser system 62 may be implemented using an Ytterbium-doped fiber laser system or some other type of laser system. Of course, in other illustrative examples, generation laser system 60 and detection laser system 62 may be implemented using some other type of laser system.

Laser beam 66 and detection laser beam 70 may be emitted from laser system 56 at an output 74. Output 74 may be the point at which laser beam 66 and detection laser beam 70 enter free space, or air. In some illustrative examples, laser beam 66 and detection laser beam 70 may be emitted through output 74 using transmission system 64. Transmission system 64 may be configured to guide laser beam 66 and detection laser beam 70 from generation laser system 60 and detection laser system 62, respectively, to output 74. Transmission system 64 may take a number of different forms. In one illustrative example, transmission system 64 takes the form of, for example, without limitation, a waveguide, a series of connected waveguides, a fiber optic system, or some other type of structure. When transmission system 64 is used, output 74 of laser system 56 may be the output of transmission system 64.

Laser system 56 may be positioned relative to test specimen 30 (e.g., composite structure 10) such that output 74 of laser system 56 is positioned to access an area 76 of composite structure 10. In some examples, area 76 may be an area to which access is limited. For example, area 76 may be a bay, a compartment, a hollow portion, a cavity, or some other type of limited-access area of composite structure 10. In other examples, area 76 may be an area to which access is not limited and/or area 76 simply may correspond to a starting location for performing a laser ultrasound scan of some or all of composite structure 10. First portion 46 and second portion 48 of composite structure 10 of FIG. 1 are examples of area 76.

Laser ultrasound device 54 may be located outside of area 76 or within area 76, depending on, for example, the relative size and configuration of area 76 compared to the size of laser ultrasound device 54. In some examples, a portion of laser ultrasound device 54 may be positioned outside of area 76, while another portion of laser ultrasound device 54 may be positioned within area 76. For example, area 76 may be a bay within a wing box of a wing for an aircraft. Laser system 56 may be unable to enter this bay, though a mobile platform 78 of laser ultrasound device 54 may be able to be moved into or positioned within area 76. Mobile platform 78 may be any type of platform capable of movement. In one illustrative example, mobile platform 78 may take the form of robotic vehicle 80, such as crawler system 44. In some examples, projection system 58 may be associated with (e.g., coupled to or positioned on) mobile platform 78. In some examples, laser system 56 may be associated with mobile platform 78.

Whether positioned on mobile platform 78 or not, laser system 56 may be positioned such that output 74 of laser system 56 is positioned with respect to area 76 such that laser beam 66 and detection laser beam 70 are directed into or towards area 76. Projection system 58 may be configured to receive laser beam 66 and detection laser beam 70. Further, projection system 58 may be configured to project laser beam 66 and detection laser beam 70 onto surface 38 of composite structure 10 within area 76. In some examples, projection system 58 projects laser beam 66 and detection laser beam 70 onto or at the same location on surface 38. In other examples, laser beam 66 and detection laser beam 70 may be projected onto different locations on surface 38. Projection system 58 may be implemented in a number of different ways. For example, projection system 58 may be implemented using at least one of a mirror, a prism, a lens, a rotating diffraction grating, a mirror-based gimbal system, a beam-director unit, a galvanometer, a mirror galvanometer, a galvanometer scanner, or some other type of device.

In some illustrative examples, laser ultrasound device 54 includes alignment system 50, which may be configured to ensure that laser beam 66 and detection laser beam 70 emitted through output 74 are received by projection system 58. In other words, alignment system 50 may be configured to align laser beam 66 and detection laser beam 70 with projection system 58. This type of alignment may require one or more changes in the direction of the path for laser beam 66 and/or detection laser beam 70. Additionally or alternatively, alignment system 50 may be configured to ensure that laser beam 66 and detection laser beam 70 are projected onto surface 38 at the desired location or locations. Alignment system 50 may be implemented in a number of different ways. For example, alignment system 50 may include at least one of a mirror, a prism, a lens, a rotating diffraction grating, a mirror-based gimbal system, a beam-director unit, a galvanometer, a mirror galvanometer, a galvanometer scanner, a detector, a quadrant cell detector, and/or some other type of device. In some examples, at least a portion of alignment system 50 may be associated with mobile platform 78. In some examples, at least a portion of alignment system 50 may be associated with another platform located within area 76. This other platform may be configured to remain stationary within area 76 during inspection or testing of composite structure 10, or may be capable of movement within area 76.

In response to laser beam 66 impacting surface 38, a number of ultrasonic waves 82, or stress waves 82, may be formed within composite structure 10. Ultrasonic waves 82 may be detected using detection system 52 and detection laser beam 70. For example, when detection laser beam 70 encounters at least one ultrasonic wave 82, detection laser beam 70 may be altered. The alteration may include a change in at least one of the path, intensity, phase, frequency, or some other feature of detection laser beam 70. Any alterations to detection laser beam 70 may be detected using detection system 52. Detection system 52 may be configured to detect a signal 83 from one or more detection points on surface 38 of test specimen 30, with the signal corresponding to the altered detection laser beam 70 at the given respective locations. Information (e.g., signals 83) may be collected at one or more detection points via, for example, reflection or through-transmission in some systems 28. In one illustrative example, detection system 52 takes the form of an interferometry-based detection system.

In some examples, at least a portion of detection system 52 may be associated with mobile platform 78. In some examples, at least a portion of detection system 52 may be associated with another platform located within area 76. This other platform may be configured to remain stationary within area 76 during inspection or testing of composite structure 10, or may be capable of movement within area 76. In some examples, laser system 56 and detection system 52 may be associated with a platform located remotely with respect to area 76 of composite structure 10.

Detection system 52 generates data 84 in response to the detection of detection laser beam 70 (e.g., in response to information such as signal 83). Data 84 may be used to identify information about composite structure 10. For example, control unit 34 may be configured to receive data 84 from detection system 52 and then filter, process, store, and/or display information about composite structure 10. This information may include, for example, without limitation, a thickness of composite structure 10, a material composition of composite structure 10, an indication of whether any undesired inconsistencies are present on and/or in composite structure 10, and/or other types of information.

Laser system 56, projection system 58, detection system 52, and/or alignment system 50 may be controlled using control unit 34. Control unit 34 may be implemented using hardware, software, or a combination of the two. In one illustrative example, control unit 34 may be implemented within a computer system comprising one or more computers. When more than one computer is present in the computer system, these computers may be in communication with each other. In another illustrative example, control unit 34 may be implemented using one or more processors, a multi-processor core, and/or some other type of processor, depending on the implementation. Additionally or alternatively, control unit 34 may be implemented using a circuit system, an application specific integrated circuit (ASIC), a programmable logic device, or some other suitable type of hardware unit. A portion of control unit 34 is associated with laser system 56 in some examples. Additionally or alternatively, a portion of control unit 34 may be associated with mobile platform 78. For example, a portion of control unit 34 may be integrated in the controller for robotic vehicle 80. In some examples, at least a portion of control unit 34 is implemented separately from laser system 56, mobile platform 78, projection system 58, and/or detection system 52. In these examples, laser system 56, mobile platform 78, projection system 58, and/or detection system 52 may be configured to receive commands from and/or send data 84 to control unit 34 using a number of communications links. These communications links may include, for example, without limitation, a number of wired communications links, a number of wireless communications links, a number of optical communications links, and/or other types of communications links.

Control unit 34 may be configured to control the movement of mobile platform 78, such as movement of mobile platform 78 within area 76 or with respect to area 76. Control unit 34 may use, for example, without limitation, an image, a scan, a computer-aided design (CAD) model, and/or other types of data for composite structure 10 to generate commands for guiding mobile platform 78. In some cases, control unit 34 may use data received from a positioning system 86 to guide and/or instruct movement of mobile platform 78 and/or other components of laser ultrasound device 54. In one illustrative example, at least a portion of positioning system 86 is associated with mobile platform 78. Positioning system 86 may include, for example, without limitation, a laser device, an imaging system, a motion capture system, a laser detection system, and/or other types of systems or devices that may be used to monitor the location of mobile platform 78 within or with respect to area 76 and/or composite structure 10. In this manner, the current location of mobile platform 78 (or other aspect of laser ultrasound device 54) within area 76 or with respect to composite structure 10 at any given point in time may be used to guide mobile platform 78 to a next location within area 76 or with respect to composite structure 10. In some examples, laser system 56 may be configured to move outside of composite structure 10 such that the direction in which laser beam 66 and/or detection laser beam 70 enters area 76 may be changed. In some cases, alignment system 50 may be used to change the direction in which laser beam 66 and detection laser beam 70 are directed within area 76.

Control unit 34 may be any suitable device or devices that are configured to perform the functions of the control unit or processor discussed herein. For example, the control unit may include one or more of an electronic controller, a dedicated controller, a special-purpose controller, a personal computer, a special-purpose computer, a display device, a logic device, a memory device, and/or a memory device having computer readable media suitable for storing computer-executable instructions for implementing aspects of systems and/or methods according to the present disclosure.

Testing environment 45 may include other components in addition to or in place of the ones illustrated in FIGS. 2-3. Some illustrated components are optional. Also, the blocks illustrated in FIGS. 2-3 are presented to illustrate some functional components, but one or more of these blocks may be combined, divided, or combined and divided into different blocks when implemented in various embodiments.

Figure 4:
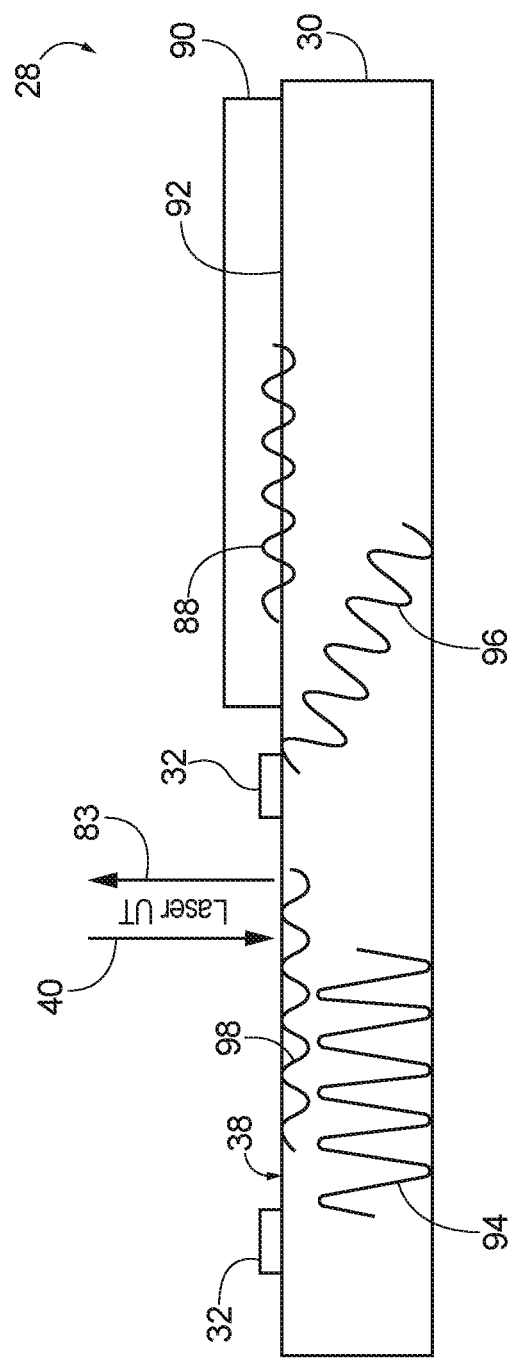
FIG. 4 is a schematic illustration of various acoustical waves interrogating the surface of a test specimen according to methods of the present disclosure.

Turning now to FIG. 4, systems 28 may include one or more NDI sensors 32 coupled to test specimen 30 that are configured to generate acoustical waves for interrogating specific types of defects or stress effects in test specimen 30. For example, one or more NDI sensors 32 may be configured to generate an interface wave 88 (e.g., a Stoneley wave) for interrogating a bondline 92, such as a bondline 92 where a portion 90 of test specimen 30 is bonded to surface 38. Additionally or alternatively, one or more NDI sensors 32 may be configured to generate a lamb wave 94 for interrogating impact-induced delamination, disbonds, and/or cracks in test specimen 30. Additionally or alternatively, one or more NDI sensors 32 may be configured to generate a shear vertical wave 96 for interrogating skewed defects in test specimen 30. Additionally or alternatively, one or more NDI sensors 32 may be configured to generate a surface wave 98 (e.g., a Rayleigh wave) for interrogating microcracking and/or other surface damage to test specimen 30. In various examples, different frequencies of waves may be generated by one or more NDI sensors 32, as desired. In some examples, the frequency generated by a respective NDI sensor 32 may be altered during the course of mechanical testing or inspection of test specimen 30. In some examples, a given NDI sensor 32 may be configured to generate such acoustic waves only at certain times during mechanical testing or inspection of test specimen. In some examples, system 28 may be configured such that one or more respective NDI sensors 32 may selectively generate an acoustical wave during testing of the test specimen, in one or more selected locations or regions of test specimen 30. For example, one or more respective NDI sensors 32 positioned near or within regions of detected damage or stress effects in test specimen 30 may be configured to selectively generate an acoustical wave when such stress effects or damage are detected, such as to further interrogate or characterize said stress effects or damage.

Figure 5:
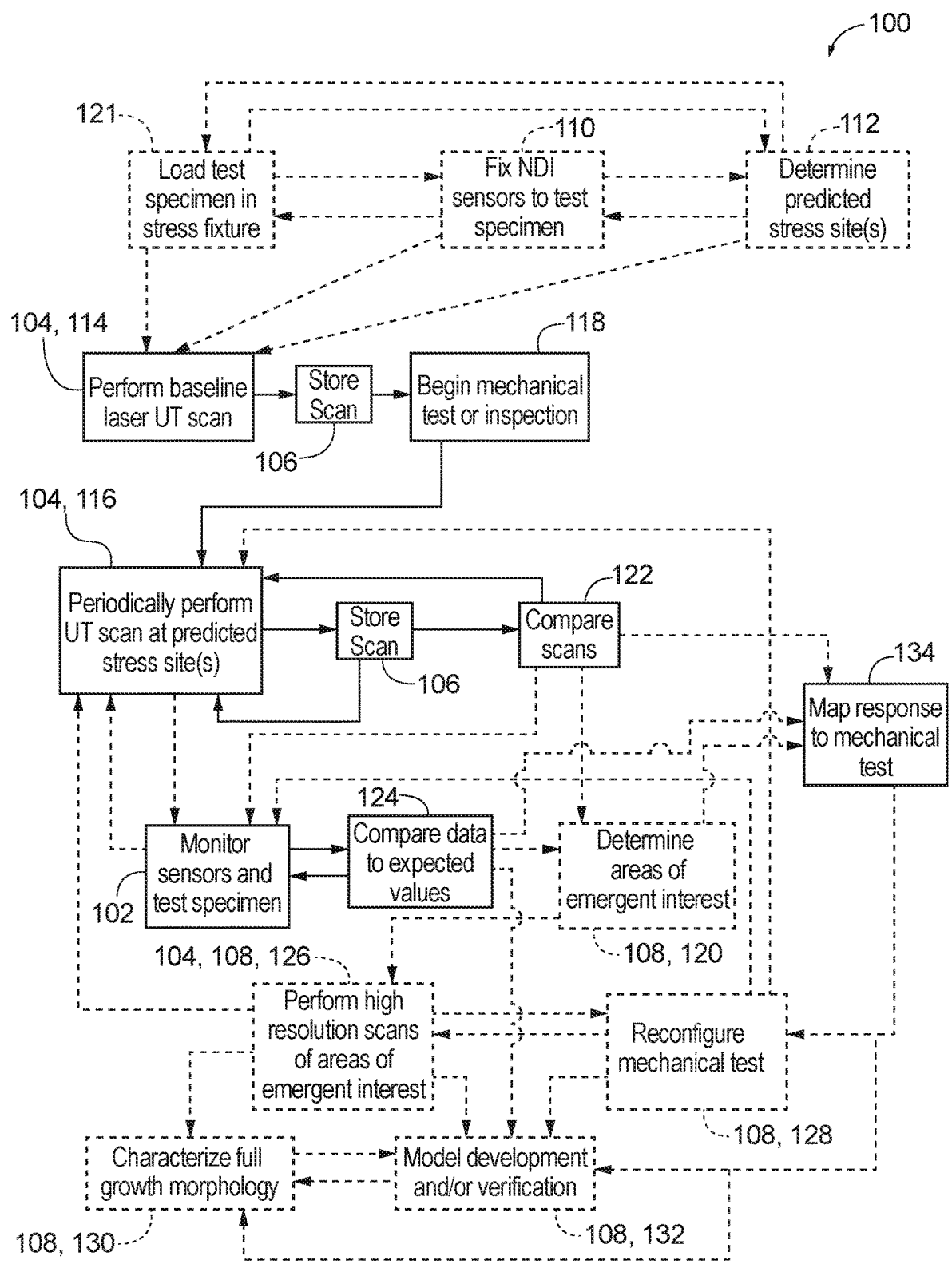
FIG. 5 is a schematic flowchart diagram of methods of testing a composite structure according to the present disclosure.

FIG. 5 schematically provides a flowchart that represents illustrative, non-exclusive examples of methods 100 for testing and/or inspecting a test specimen according to the present disclosure. In FIG. 5, some steps are illustrated in dashed boxes indicating that such steps may be optional or may correspond to an optional version of a method according to the present disclosure. That said, not all methods according to the present disclosure are required to include the steps illustrated in solid boxes. The methods and steps illustrated in FIG. 5 are not limiting and other methods and steps are within the scope of the present disclosure, including methods having greater than or fewer than the number of steps illustrated, as understood from the discussions herein.

Methods 100 for testing and/or inspecting a test specimen (e.g., test specimen 30) generally include monitoring the test specimen at 102, scanning at least a portion of the test specimen using a laser ultrasound device (e.g., laser ultrasound device 31) at 104, thereby producing a laser ultrasound scan of stress effects within the test specimen, storing the laser ultrasound scan at 106, and integrating scan data from the laser ultrasound scan with fixed sensor data from one or more NDI sensors (e.g., NDI sensors 32) fixed with respect to the test specimen, at 108. As the phrase is used herein, "integrating" scan data from the laser ultrasound scan with fixed sensor data from one or more NDI sensors means using, analyzing, processing, filtering, and/or storing data from both laser ultrasound scans and NDI sensors to monitor and/or inspect a test specimen. Resultant integrated scans or images incorporate data from all sources (e.g., scan data and fixed sensor data), thereby integrating data from multiple sources into a coherent whole. According to presently disclosed methods 100, the test specimen may be monitored for damage in real-time.

Monitoring the test specimen at 102 generally includes monitoring fixed sensor data from the one or more NDI sensors fixed with respect to the test specimen. The NDI sensors are configured to monitor indications of damage in or on the test specimen, and further configured to produce fixed sensor data related to the test specimen. One or more of the fixed NDI sensors may be mounted on or to the test specimen itself. Additionally or alternatively, one or more of the fixed NDI sensors may be fixed with respect to the test specimen at a location spaced apart from the test specimen. In other words, the fixed NDI sensors may include one or more wide-field stand-off sensors, which may include thermography sensors, x-ray sensors, PZT transducers, phased array sensors, and/or acoustic emission sensors, among others. Some methods 100 include mounting one or more NDI sensors to the test specimen at 110. In some examples, fixed NDI sensors may be mounted at 110 at locations on the test specimen that have been predicted to experience the greatest stresses, and/or that have been predicted to experience the most damage when the test specimen is stressed and/or used. Some methods include determining these predicted locations at 112, which may be performed before mounting the NDI sensors at 110, in some examples. Mounting NDI sensors at 110 may include mounting or securing a plurality of different types of NDI sensors, in some methods 100. Generally, such monitoring of NDI sensors at 102 is performed throughout a mechanical test of the test specimen.

Scanning at least a portion of the test specimen at 104 may include both performing a baseline scan of the test specimen at 114 and also periodically scanning the test specimen at 116. Generally, the performing the baseline scan at 114 is performed before beginning a mechanical test or inspection of the test specimen at 118 (e.g., the baseline scan may be performed at 114 while the test specimen is not stressed or loaded, in some examples). Performing the baseline scan at 114 generally includes scanning the entire test specimen using the laser ultrasound device, though in some examples, just a portion of the test specimen may be scanned for the baseline scan at 114. After the mechanical test or inspection of the test specimen is initiated at 118, periodic scans at 116 are generally performed on just a portion of the test specimen, through some or all of the periodic scans may be performed on the entire test specimen during mechanical testing. The periodic scans performed at 116 may be focused on locations of the test specimen that are predicted to experience the greatest stresses or the highest risks of damage, in some methods 100. Additionally or alternatively, the periodic scans performed at 116 may be focused on locations of the test specimen corresponding to areas of emergent interest determined (at 120) during the testing or inspection of the test specimen. In some methods 100, the periodic laser ultrasound scans performed at 116 may be automated, and may be taken of a predetermined area or region of the test specimen, and/or of areas identified during testing or inspection of the test specimen. For example, performing periodic laser ultrasound scans at 116 may include configuring a crawler system (e.g., crawler system 44) and/or a mobile platform (e.g., mobile platform 78) to position the laser ultrasound device for performing the periodic laser ultrasound scans of the test specimen at 116.

Each respective laser ultrasound scan performed at 116 produces a respective laser ultrasound scan that is stored at 106, with such scans providing spatial information corresponding to stress effects at different locations of the test specimen. Laser ultrasound scans may be performed periodically at 116 throughout mechanical testing or inspection of the test specimen.

Mechanically testing the test specimen at 118 may include testing the test specimen via any suitable testing method. For example, mechanically testing the test specimen at 118 may include mechanically stressing or loading the test specimen, a bent wing test for a wing of an aircraft, periodically flexing the test specimen, subjecting the test specimen to one or more fatigue cycles, bending the test specimen to its limit load, static loading, fatigue loading, applying an external load to the test specimen, pressurizing the test specimen, and/or internally interrogating the test specimen (e.g., generating a low-frequency load via one or more onboard transducers fixed to the test specimen). Some methods 100 include loading the test specimen into a stress fixture (e.g., mechanical stress fixture 42) or other testing fixture at 121, with the stress fixture being configured to position and/or move the test specimen during mechanical testing of the test specimen at 118. In some examples, the test specimen is held in a static condition during mechanical testing at 118. Testing the test specimen at 118 may include full scale, mid-scale, and/or sub-scale mechanical testing (e.g., for analysis validation), manufacturing inspections, and/or in-service inspections.

Monitoring the test specimen at 102 may include monitoring fixed sensor data from the fixed NDI sensors. For example, monitoring the test specimen at 102 may include collecting the fixed sensor data, filtering the fixed sensor data, processing the fixed sensor data, storing the fixed sensor data, and/or displaying the fixed sensor data. In some methods 100, monitoring the test specimen and fixed NDI sensors at 102 includes monitoring for acoustic emission events from an unexpected area of the test specimen, monitoring for a plate or surface wave showing cracking in an unexpected area of the test specimen, monitoring thermography images, monitoring a video image of surface damage to the test specimen, digital image correlation, and/or monitoring a full-field strain image for indications of sub-surface damage to the test specimen. Such damage indications may be measured, identified, and/or tracked in real time. Additionally or alternatively, monitoring the test specimen and fixed NDI sensors at 102 may include monitoring one or more stand-off wide-field sensors for any signal that differs from expectations or in areas not predicted to have the greatest stress effects.

During mechanical testing of the test specimen at 118, respective laser ultrasound scans are compared at 122, and fixed sensor data from NDI sensors is compared to expected values from those sensors at 124. For example, comparing laser ultrasound scans at 122 may include comparing a respective laser ultrasound scan with one or more previous laser ultrasound scans, to determine differences between the scans that correspond to changes within the test specimen due to stress effects. In some methods 100, comparing laser ultrasound scans at 122 includes image subtraction. Additionally or alternatively, comparing laser ultrasound scans at 122 may include identifying areas where the structure of the test specimen is changing over time (e.g., identifying the locations of the test specimen that correspond to those changes identified by comparing laser ultrasound scans at 122). Comparing laser ultrasound scans at 122 may be performed in real-time. In some examples, comparing laser ultrasound scans at 122 may include monitoring and/or examining the laser ultrasound scans for oddly-shaped areas that may indicate defects, and/or for areas of depth mismatch compared to surrounding areas of the test specimen.

Monitoring the test specimen and associated fixed NDI sensors at 102 may include identifying locations of the test specimen corresponding to fixed sensor data from a respective fixed NDI sensor that differs from expected signal values (e.g., exceeds expected signal values or is less than expected signal values), based on comparing fixed sensor data to expected values at 124. In some methods 100, such comparisons will locate unexpected areas (e.g., areas not predicted by stress analysis) of the test specimen experiencing higher than expected stress effects, with such unexpected areas also being referred to herein as emergent areas of interest. Monitoring the test specimen and sensors at 102, comparing fixed sensor data to expected values at 124, and/or comparing different laser ultrasound scans with each other at 122 is automated or semi-automated in some methods 100. Such expected values from fixed NDI sensors and expected stress sites may be predetermined at 112 in some methods 100.

An emergent area of interest may be determined at 120 based on data from comparing laser ultrasound scans at 122, such as if the laser ultrasound scans show damage propagation in an unexpected area of the test specimen or higher than expected stress effects. Similarly, an emergent area of interest may be determined at 120 based on comparing data from fixed NDI sensors with expected values at 124, such as if fixed sensor data has a higher than expected value for a given location of the test specimen. In some examples, comparing fixed sensor data to expected values at 124 may include using fixed NDI sensors to generate specific types (e.g., frequencies) of acoustical waves configured to interrogate the test specimen for different types of damage or stress effects. For example, comparing fixed sensor data to expected values at 124 may include generating interface waves (e.g., Stoneley waves) to interrogate bondlines of the test specimen, generating surface waves (e.g., Rayleigh waves) to interrogate micro-cracking and/or surface damage to the test specimen, generating lamb waves to interrogate impact-induced delamination, disbonds, and/or cracks in the test specimen, and/or generating shear vertical waves to interrogate skewed defects in the test specimen. In some methods 100, determining areas of emergent interest at 120 may be based on both data from comparing laser ultrasound scans at 122 and from comparing fixed sensor data to expected values at 124, thus integrating data from laser ultrasound scans and from fixed NDI sensors to monitor the test specimen at 108.

In some methods, determining one or more emergent areas of interest at 120 may include determining the emergent area(s) of interest via triangulation based on data from a plurality of fixed NDI sensors. Additionally or alternatively, determining one or more emergent areas of interest at 120 may include identifying one or more differences between a first respective laser ultrasound scan and a second respective laser ultrasound scan performed on the test specimen before or after the first respective laser ultrasound scan.

Generally, scanning the test specimen at 104 includes creating an area of local heating expansion within the test specimen by generating (e.g., emitting) and directing a laser beam at the test specimen (e.g., towards an emergent area of interest, and/or towards an area of predicted failure or stress effects) using the laser ultrasound device, thereby generating a resulting ultrasound wave or waves that travels through or across the surface of the test specimen. Scanning the test specimen at 104 also generally includes generating (e.g., emitting) a detection laser beam (e.g. from the laser ultrasound device), projecting or directing the detection laser beam onto or towards a surface of the test specimen, and detecting alterations of the detection laser beam caused by the ultrasonic waves in the test specimen. In some examples, scanning the test specimen at 104 includes performing a pulse-echo laser ultrasound scan. In some methods 100, scanning the test specimen at 104 may include performing one or more high density full-waveform scans of at least a portion of the test specimen. Scanning the test specimen at 104 may include aligning the laser beam via an alignment system, such that the laser beam is directed to a desired location of the test specimen.

Systems 28 according to the present disclosure integrate data from laser ultrasound scans and from NDI sensors at 108 to monitor and inspect the test specimen at 102, 118. Integrating data from laser ultrasound scans and fixed NDI sensors at 108 (e.g., scanning the test specimen at 104, comparing scans at 122, monitoring sensors at 102, comparing fixed sensor data to expected values at 124, and/or determining emergent areas of interest at 120) may include detecting and monitoring damage initiation and/or growth within the test specimen. Some systems 28 are configured to characterize full damage growth morphology without time-consuming stoppage of the mechanical test or movement of NDI sensors 32. In some examples, integrating data from laser ultrasound scans and fixed NDI sensors at 108 may include detecting such damage throughout an entire depth of the test specimen. Additionally or alternatively, integrating data from laser ultrasound scans and fixed NDI sensors at 108 may include detecting such damage through just a portion of the depth of the test specimen and/or on the surface of the test specimen. In some presently disclosed methods 100, integrating data from laser ultrasound scans and fixed NDI sensors at 108 may include detecting damage or defects on the micro scale and/or on the macro scale. In some examples, integrating data from laser ultrasound scans and fixed NDI sensors at 108 may include determining a general area of a stress effect within the test specimen using data from fixed NDI sensors, and then locating the stress effects with greater accuracy using a laser ultrasound scan of the general area, without needing to stop the mechanical test.

In some examples, scanning the test specimen at 104 includes performing a high-resolution laser ultrasound scan of one or more emergent areas of interest may be performed at 126. In some methods, performing a baseline laser ultrasound scan at 114 may include a high-resolution scan, and/or one or more of the periodic scans performed at 116 may be a high-resolution scan. In some methods, one or more of the laser ultrasound scans performed at 104, 114, 116, and/or 126 may be performed at a lower or higher resolution than one or more other of the laser ultrasound scans performed in presently disclosed methods. In other words, methods 100 may include varying the resolution of the laser ultrasound scans performed during a given mechanical test or inspection. For example, one or more of the periodic scans performed at 116 may be performed at a lower resolution than are one or more of the high-resolution scans of emergent area(s) of interest performed at 126. As the term is used herein, "high-resolution" refers to a laser ultrasound scan having a spatial resolution of less than 80 mil (0.08 inches (in), or 2.03 millimeters (mm)), less than 70 mil (0.070 in; 1.778 mm), less than 60 mil (0.060 in; 1.524 mm), less than 50 mil (0.050 in; 1.27 mm), less than 40 mil (0.040 in; 1.016 mm), less than 30 mil (0.030 in; 0.762 mm), less than 20 mil (0.020 in; 0.508 mm), less than 10 mil (0.010 in; 0.254 mm), and/or less than 5 mil (0.005 in; 0.127 mm). Each high-resolution scan, including high-resolution scans of emergent areas of interest at 126, may be stored for future access and/or analysis. Performing one or more high-resolution scans of emergent areas of interest at 126 is another example of integrating data from fixed NDI sensors and laser ultrasound scans at 108.

As further examples of integrating data from fixed NDI sensors and laser ultrasound scans of the test specimen, some methods 100 may include reconfiguring the mechanical test at 128, characterizing growth morphology at 130, model development and/or verification at 132, and/or mapping an overall response of the test specimen to being mechanically tested (e.g., stressed) at 134. In some methods 100, the full growth morphology of a damage indication at 130 may be characterized without interrupting the mechanical testing of the test specimen and/or without moving the fixed NDI sensors (which can be time-consuming and/or invalidate the test). For example, integrating data from fixed NDI sensors and laser ultrasound scans at 108 may allow for identification of a damage indication in the test specimen and focusing of one or more subsequent laser ultrasound scans performed to the identified damaged area for further monitoring. Because the laser ultrasound device is non-contact (e.g., generally the laser ultrasound device is not fixed to the test specimen), moving or directing the laser ultrasound device to a different location can be performed without affecting the mechanical testing of the test specimen. In some examples, the mechanical testing of the test specimen may be reconfigured or altered at 128 to accommodate emergent indications of damage within the test specimen without interrupting the testing. For example, changes may be made to the frequency, resolution, and/or areas in which laser ultrasound scans are performed during the testing. Additionally or alternatively, reconfiguring the mechanical testing at 128 may include altering the frequency of acoustical waves generated by onboard transducers (e.g., one or more of the fixed NDI sensors) for interrogating different aspects of the test specimen, in response to emergent indications of damage, and/or changing the geometries of placement of NDI sensors 32.

Methods 100 may be performed at any stage of the manufacturing process. For example, methods 100 may be used to examine and/or inspect a test specimen for manufacturing defects. Methods 100 may be used to compare in-service (e.g., assembled) parts with the as-built record taken during the original manufacturing process (e.g., inspecting the in-service part).

Figure 6:
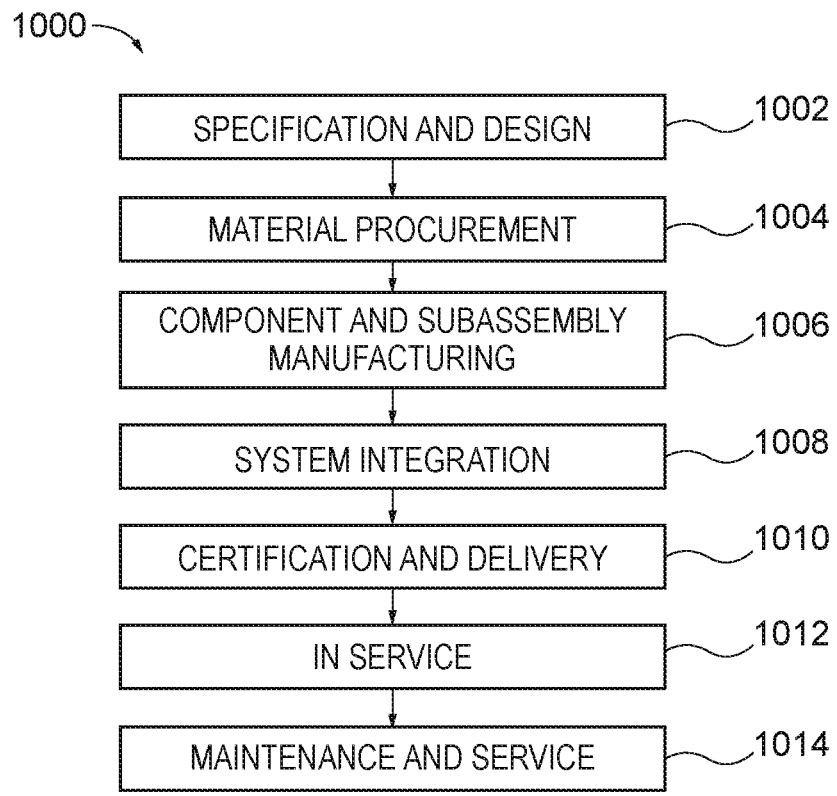
FIG. 6 is a block diagram illustrating methods of aircraft manufacturing and service.
Figure 7:
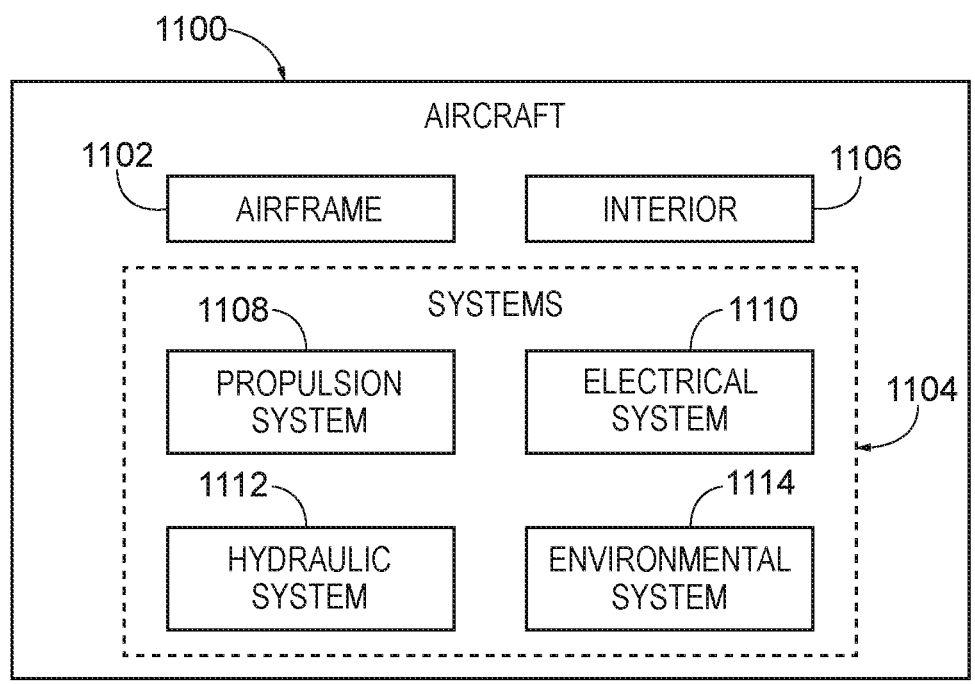
FIG. 7 is a block diagram illustrating an aircraft.

Illustrative embodiments of the disclosure may be described in the context of aircraft manufacturing and service method 1000, as shown in FIG. 6, and aircraft 1100 (which is an example of aircraft 14), as shown in FIG. 7. Turning first to FIG. 6, an illustration of an aircraft manufacturing and service method is depicted in the form of a block diagram in accordance with an illustrative embodiment. During pre-production, aircraft manufacturing and service method 1000 may include specification and design at 1002 of aircraft 1100 of FIG. 7, and material procurement at 1004. During production, component and subassembly manufacturing at 1006 and system integration at 1008 of aircraft 1100 of FIG. 7 takes place. Thereafter, aircraft 1100 of FIG. 7 may go through certification and delivery at 1010 in order to be placed in service at 1012. While in service at 1012 by a customer, aircraft 1100 of FIG. 7 may be scheduled for routine maintenance and service at 1014, which may include modification, reconfiguration, refurbishment, and other maintenance or service.

Each of the processes of aircraft manufacturing and service method 1000 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 7, an illustration of an aircraft is depicted in the form of a block diagram in which an illustrative embodiment may be implemented. In this example, aircraft 1100 is produced by aircraft manufacturing and service method 1000 of FIG. 6, and may include an airframe 1102 with systems 1104 and an interior 1106. Examples of systems 1104 include one or more of a propulsion system 1108, an electrical system 1110, a hydraulic system 1112, and an environmental system 1114. Any number of other systems may be included. Although an aerospace example is shown, different illustrative embodiments may be applied to other industries, such as the automotive industry.

Systems and methods embodied herein may be employed during at least one of the stages of aircraft manufacturing and service method 1000 of FIG. 6. For example, a laser ultrasound testing system, such as laser ultrasound device 31 of FIG. 2, may be used to inspect various components of aircraft 1100 during one or more of the stages of aircraft manufacturing and service method 1000 of FIG. 6. In particular, laser ultrasound device 31 may be used to inspect components of aircraft 1100 during component and subassembly manufacturing at 1006, system integration at 1008, certification and delivery at 1010, in service at 1012, routine maintenance and service at 1014, and/or some other stage of aircraft manufacturing and service method 1000.

In one illustrative example, components or subassemblies produced in component and subassembly manufacturing at 1006 of FIG. 6 may be fabricated or manufactured in a manner similar to components or subassemblies produced while aircraft 1100 is in service at 1012 in FIG. 6. As yet another example, one or more disclosed systems, methods, or a combination thereof may be utilized during production stages, such as component and subassembly manufacturing at 1006 and system integration at 1008 in FIG. 6. Additionally or alternatively, one or more disclosed systems, methods, or a combination thereof may be utilized while aircraft 1100 is in service at 1012 and/or during maintenance and service at 1014 in FIG. 6. The use of a number of the different illustrative examples may, in some examples, substantially expedite the assembly of and/or reduce the cost of aircraft 1100.

The flowcharts and block diagrams in the different depicted examples illustrate the architecture, functionality, and operation of some possible implementations of apparatuses and methods in an illustrative example. In this regard, each block in the flowcharts or block diagrams may represent a module, a segment, a function, and/or a portion of an operation or step. For example, one or more of the blocks may be implemented as program code, in hardware, or a combination of the program code and hardware. In some alternative implementations of an illustrative example, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

The description of the different illustrative examples has been presented for purposes of illustration and description, and is not intended to be exhaustive or limited to the embodiments in the form disclosed. Many modifications and variations will be apparent to those of ordinary skill in the art. Further, different illustrative examples may provide different features as compared to other desirable examples. The example or examples selected are chosen and described in order to explain the principles of the examples, the practical application, and to enable others of ordinary skill in the art to understand the disclosure for various examples with various modifications as are suited to the particular use contemplated.

As used herein, the terms "selective" and "selectively," when modifying an action, movement, configuration, or other activity of one or more components or characteristics of an apparatus, mean that the specific action, movement, configuration, or other activity is a direct or indirect result of user manipulation of an aspect of, or one or more components of, the apparatus.

Illustrative, non-exclusive examples of inventive subject matter according to the present disclosure are described in the following enumerated paragraphs:

A1. A method of testing and/or inspecting a test specimen, the method comprising:

monitoring the test specimen with a fixed non-destructive inspection (NDI) sensor fixed with respect to the test specimen, wherein the NDI sensor is configured to monitor indications of damage in or on the test specimen, and wherein the NDI sensor is configured to produce fixed sensor data related to the test specimen;

scanning at least a portion of the test specimen using a laser ultrasound device, thereby producing a first laser ultrasound scan of stress effects within the test specimen;

storing the first laser ultrasound scan; and integrating scan data from the first laser ultrasound scan with the fixed sensor data from the NDI sensor.

A1.1 The method of paragraph A1, wherein the laser ultrasound device is positioned apart from the test specimen.

A1.2. The method of paragraph A1 or A1.1, wherein the laser ultrasound device is positioned outside of the at least the portion of the test specimen being scanned.

A1.3. The method of any of paragraphs A1-A1.2, further comprising mounting the NDI sensor to the test specimen.

A1.4. The method of any of paragraphs A1-A1.3, comprising mounting a plurality of NDI sensors to the test specimen.

A2. The method of any of paragraphs A1-A1.4, wherein the scanning is performed at least once before mechanically testing the test specimen.

A3. The method of any of paragraphs A1-A2, wherein the scanning is performed a plurality of times, thereby producing a plurality of respective laser ultrasound scans.

A4. The method of paragraph A3, wherein the scanning is performed both before mechanically testing the test specimen and at least once during mechanically testing the test specimen.

A4.1. The method of paragraph A3, wherein the scanning is performed periodically while mechanically testing the specimen.

A5. The method of any of paragraphs A3-A4.1, wherein the first laser ultrasound scan is a baseline scan that is produced by performing the scanning before mechanically testing the specimen, and wherein each subsequent performance of the scanning produces a respective subsequent laser ultrasound scan.

A5.1. The method of paragraph A5, wherein the storing the first laser ultrasound scan comprises storing the baseline scan and storing each respective subsequent laser ultrasound scan.

A6. The method of any of paragraphs A1-A5.1, wherein at least one performance of the scanning comprises scanning an entirety of the test specimen.

A7. The method of any of paragraphs A1-A6, wherein at least one performance of the scanning comprises scanning a first portion of the test specimen corresponding to a location of predicted stress sites.

A8. The method of any of paragraphs A1-A7, wherein at least one performance of the scanning comprises scanning a second portion of the test specimen corresponding to an emergent area of interest.

A9. The method of paragraph A8, wherein the emergent area of interest is determined by comparing a first respective laser ultrasound scan produced by a respective performance of the scanning with a second respective laser ultrasound scan produced by a later respective performance of the scanning.

A10. The method of any of paragraphs A1-A9, wherein the scanning comprises producing a high density full-waveform scan.

A11. The method of any of paragraphs A1-A10, further comprising mapping a response of the test specimen to being mechanically tested.

A12. The method of any of paragraphs A1-A11, further comprising determining one or more emergent areas of interest.

A13. The method of paragraph A12, wherein the determining the one or more emergent areas of interest comprises triangulating based on data from one or more NDI sensors.

A14. The method of paragraph A12 or A13, wherein the scanning comprises scanning at a first time, thereby producing the first respective laser ultrasound scan, and scanning at a second time later than the first time, thereby producing the second respective laser ultrasound scan, and wherein the determining the one or more emergent areas of interest comprises comparing the first respective laser ultrasound scan and the second respective laser ultrasound scan to determine differences between the first respective laser ultrasound scan and the second respective laser ultrasound scan.

A15. The method of paragraph A14, comprising repeating the scanning a plurality of times to produce a plurality of respective laser ultrasound scans, and repeating the comparing a plurality of times to compare each of the plurality of respective laser ultrasound scans with one or more previous respective laser ultrasound scans.

A16. The method of paragraph A15, wherein the storing the first laser ultrasound scan comprises storing each of the plurality of respective laser ultrasound scans.

A17. The method of any of paragraphs A14-A16, wherein the comparing comprises image subtraction.

A18. The method of any of paragraphs A14-A17, wherein the comparing comprises identifying areas where the structure of the test specimen is changing.

A19. The method of any of paragraphs A12-18, further comprising performing a high-resolution laser ultrasound scan of each of the one or more emergent areas of interest.

A20. The method of paragraph A19, further comprising storing results from the high-resolution laser ultrasound scan of each of the one or more emergent areas of interest.

A21. The method of paragraph A19 or A20, wherein the scanning to produce the first laser ultrasound scan is performed at a first resolution, wherein the performing the high-resolution laser ultrasound scan of each of the one or more emergent areas of interest is performed at a second resolution, and wherein the second resolution is greater than the first resolution.

A22. The method of paragraph A21, wherein the second resolution is at least 100 mil, at least 90 mil, at least 80 mil, at least 70 mil, at least 60 mil, at least 50 mil, at least 40 mil, at least 30 mil, at least 20 mil, and/or at least 10 mil.

A23. The method of any of paragraphs A19-A22, wherein the performing the high-resolution laser ultrasound scan comprises performing a full-waveform, pulse echo ultrasound scan.

A24. The method of any of paragraphs A1-A23, wherein the scanning using the laser ultrasound device and/or performing a/the high-resolution laser ultrasound scan of an/the one or more emergent areas of interest comprises creating an area of local heating expansion within the test specimen, thereby generating a resulting ultrasound wave.

A25. The method of any of paragraphs A1-A24, wherein the scanning using the laser ultrasound device and/or performing a/the high-resolution laser ultrasound scan of an/the one or more emergent areas of interest is performed while the test specimen is held in a static condition.

A26. The method of any of paragraphs A1-A25, wherein the scanning using the laser ultrasound device and/or performing a/the high-resolution laser ultrasound scan of an/the one or more emergent areas of interest is performed without contacting the test specimen.

A27. The method of any of paragraphs A1-A26, wherein the scanning using the laser ultrasound device and/or performing a/the high-resolution laser ultrasound scan of an/the one or more emergent areas of interest is performed and each of the plurality of respective laser ultrasound scans are analyzed and compared in real-time.

A28. The method of any of paragraphs A1-A27, further comprising configuring a crawler system to perform automated laser ultrasound scans of at least a portion of the test specimen and/or of one or more emergent areas of interest, while mechanically testing the test specimen.

A29. The method of any of paragraphs A1-A28, wherein the scanning using the laser ultrasound device and/or performing a/the high-resolution laser ultrasound scan of an/the one or more emergent areas of interest comprises:

emitting a detection laser beam from the laser ultrasound device;

projecting the detection laser beam onto a surface of the test specimen; and detecting an alteration in the detection laser beam resulting from a plurality of ultrasonic waves formed in the test specimen via the scanning and/or the performing the high-resolution laser ultrasound scan.

A30. The method of paragraph A29, wherein the projecting the detection laser beam comprises projecting the detection laser beam to one or more emergent areas of interest on the test specimen.

A31. The method of paragraph A29 or A30, wherein the detecting the plurality of ultrasonic waves is performed via the laser ultrasound device.

A32. The method of any of paragraphs A1-A31, wherein the scanning using the laser ultrasound device and/or performing a/the high-resolution laser ultrasound scan of an/the one or more emergent areas of interest includes detecting damage initiation and/or growth throughout a depth of the test specimen.

A33. The method of any of paragraphs A1-A32, wherein the scanning using the laser ultrasound device and/or performing a/the high-resolution laser ultrasound scan of an/the one or more emergent areas of interest includes detecting damage or defects on the micro and macro scale.

A34. The method of any of paragraphs A1-A33, wherein the test specimen comprises a sub-scale composite structure, a mid-scale composite structure, and/or a full-scale composite structure.

A35. The method of any of paragraphs A1-A34, wherein the NDI sensor comprises an acoustic emission sensor, a PZT transducer, an NDI sensor, an ultrasonic transducer, a bonded PZT sensor, a fiber optic sensor, a stand-off thermography system, a stress gauge, and/or a strain gauge.

A36. The method of any of paragraphs A1-A35, wherein the NDI sensor comprises a plurality of NDI sensors spaced apart on a/the surface of the test specimen.

A37. The method of paragraph A36, wherein respective NDI sensors of the plurality of NDI sensors are positioned in respective areas of the test specimen that are expected to be most likely to experience the highest stresses during use of the test specimen and/or during mechanical testing of the test specimen.

A38. The method of any of paragraphs A1-A37, wherein the NDI sensor comprises an ultrasonic transducer that produces A-scans, plate waves, and/or surface waves in the test specimen.

A39. The method of any of paragraphs A1-A38, wherein the NDI sensor comprises a plurality of different types of sensors.

A40. The method of any of paragraphs A1-A39, wherein the test specimen comprises an in-service part.

A40.1. The method of paragraph A40, further comprising inspecting the in-service part.

A41. The method of any of paragraphs A1-A40.1, wherein the NDI sensor comprises an onboard sensor for an/the in-service part.

A42. The method of any of paragraphs A1-A41, further comprising generating interface waves with the NDI sensor, such as Stoneley waves, that are configured to interrogate bondlines of the test specimen.

A43. The method of any of paragraphs A1-A42, further comprising generating surface waves with the fixed NDI sensor, such as Rayleigh waves, that are configured to interrogate micro-cracking and/or surface damage to the test specimen.

A44. The method of any of paragraphs A1-A43, further comprising generating lamb waves with the fixed NDI sensor, wherein the lamb waves are configured to interrogate impact-induced delamination, disbonds, and/or cracks in the test specimen.

A45. The method of any of paragraphs A1-A44, further comprising generating shear vertical waves with the fixed NDI sensor, wherein the shear vertical waves are configured to interrogate skewed defects in the test specimen.

A46. The method of any of paragraphs A1-A41, further comprising:

generating an acoustical wave using the NDI sensor; and
controlling a frequency of the acoustical wave.

A47. The method of any of paragraphs A1-A46, further comprising mechanically testing the test specimen via one or more testing methods.

A47.1 The method of paragraph A47, wherein the mechanically testing the test specimen comprises mechanically stressing or loading the test specimen.

A48. The method of any of paragraphs A47-A47.1, wherein the mechanically testing the test specimen comprises a bent wing test of a wing for an aircraft.

A49. The method of any of paragraphs A47-A48, wherein the mechanically testing the test specimen comprises periodically flexing the test specimen.

A50. The method of any of paragraphs A47-A49, wherein the mechanically testing the test specimen comprises subjecting the test specimen to one or more fatigue cycles.

A51. The method of any of paragraphs A47-A50, wherein the mechanically testing the test specimen comprises bending the test specimen to its limit load.

A52. The method of any of paragraphs A47-A51, wherein the mechanically testing the test specimen comprises static loading.

A53. The method of any of paragraphs A47-A52, wherein the mechanically testing the test specimen comprises fatigue loading.

A54. The method of any of paragraphs A47-A53, wherein the mechanically testing the test specimen comprises applying an external load to the test specimen and/or pressurizing the test specimen.

A55. The method of any of paragraphs A47-A54, wherein the mechanically testing the test specimen comprises internally interrogating the test specimen.

A56. The method of paragraph A55, wherein the internally interrogating the test specimen comprises generating a low-frequency load via one or more onboard transducers fixed to the test specimen.

A57. The method of any of paragraphs A1-A56, further comprising loading the test specimen into a mechanical stress fixture, wherein the mechanical stress fixture is configured to position and/or move the test specimen during mechanical testing of the test specimen.

A58. The method of any of paragraphs A1-A57, wherein the testing the test specimen comprises full scale mechanical testing for analysis validation, manufacturing inspections, and/or in-service inspections.

A59. The method of any of paragraphs A1-A58, further comprising collecting the fixed sensor data, filtering the fixed sensor data, processing the fixed sensor data, storing the fixed sensor data, and/or displaying the fixed sensor data.

A60. The method of any of paragraphs A1-A59, further comprising monitoring the fixed sensor data during the testing the test specimen.

A61. The method of paragraph A60, wherein the monitoring comprises comparing the fixed sensor data to expected signal values and identifying locations of the test specimen corresponding to fixed sensor data from a respective NDI sensor that differs from expected signal values.

A62. The method of paragraph A60 or A61, wherein the monitoring comprises monitoring for fixed sensor data that differs from expectations in an unexpected area of the test specimen.

A63. The method of any of paragraphs A60-A62, wherein the monitoring is automated.

A64. The method of any of paragraphs A60-A62, wherein the monitoring comprises monitoring for acoustic emission events from an unexpected area, monitoring for a plate or surface wave showing cracking in an unexpected area, monitoring thermography images, monitoring a video image of surface damage, digital image correlation, and/or monitoring a full-field strain image for indications of sub-surface damage.

A65. The method of any of paragraphs A1-A64, further comprising monitoring one or more stand-off wide-field sensors for any signal differing from expectations or in areas not predicted to be stress sites.

A66. The method of any of paragraphs A1-A65, further comprising measuring, identifying, and tracking damage indications in the test specimen in real-time.

A67. The method of any of paragraphs A1-A65, further comprising examining and/or inspecting the test specimen for manufacturing defects.

A68. The method of any of paragraphs A1-A67, further comprising characterizing full growth morphology of a large composite structure test specimen without interrupting the testing or moving the NDI sensors.

A69. The method of any of paragraphs A1-A68, further comprising reconfiguring and/or altering the one or more testing methods to accommodate emergent indications of damage in the test specimen.

A70. The method of paragraph A60, wherein the emergent indications of damage are located in areas of the test specimen not predicted by stress analysis.

A71. The method of any of paragraphs A1-A70, further comprising determining signal expectations for the NDI sensor and predicted stress sites within the test specimen.

A72. The method of any of paragraphs A1-A71, further comprising using information from the fixed sensor data, the first laser ultrasound scan, and any subsequent laser ultrasound scans of the test specimen for model development and verification.

A73. The method of any of paragraphs A1-A72, further comprising:
generating a laser beam via the laser ultrasound device; and
directing the laser beam towards the test specimen, wherein the laser beam produces a/the plurality of ultrasonic waves within the test specimen.

A74. The method of paragraph A73, wherein the directing the laser beam towards the test specimen comprises directing the laser beam towards one or more emergent areas of interest within the test specimen.

A75. The method of any of paragraphs A73-A74, further comprising aligning the laser beam via an alignment system, such that the laser beam is directed to a desired location of the test specimen.

A76. The method of any of paragraphs A73-A75, further comprising:
generating a detection laser beam via the laser ultrasound device; and
measuring an alteration in the detection laser beam caused by the plurality of ultrasonic waves.

A77. The method of any of paragraphs A1-A76, further comprising varying the resolution of the laser ultrasound scans performed during a given mechanical test or inspection.

B1. A system for testing and/or inspecting a test specimen, the system comprising:
the test specimen;
a laser ultrasound device located apart from the test specimen, wherein the laser ultrasound device is configured to generate and direct a laser beam at the test specimen, thereby producing a plurality of ultrasonic waves within the test specimen, wherein the laser ultrasound device is further configured to produce a detection laser beam and measure an alteration in the detection laser beam as a result of the plurality of ultrasonic waves, and wherein the laser ultrasound device is further configured to scan at least a portion of the test specimen and produce a laser ultrasound scan of stress effects within the test specimen;
a plurality of NDI sensors fixed to the test specimen; and
a processor configured to integrate and/or monitor data from the plurality of NDI sensors and from the laser ultrasound scan produced by the laser ultrasound device in order to monitor or inspect the test specimen.

B2. The system of paragraph B1, further comprising one or more stand-off wide-field sensors positioned away from the test specimen, wherein the stand-off wide-field sensors are configured to provide additional information about stress effects within the test specimen to the processor.

B3. The system of any of paragraphs B1-B2, further comprising a mechanical stress fixture configured to mechanically test the test specimen.

B4. The system of paragraph B3, wherein the mechanical stress fixture is configured to perform a bent wing test of a wing for an aircraft, periodically flex the test specimen, subject the test specimen to one or more fatigue cycles, bend the test specimen to its limit load, statically load the test specimen, apply an external load to the test specimen, pressurize the test specimen, internally interrogate the test specimen, position the test specimen during mechanical testing, and/or move the test specimen during mechanical testing of the test specimen.

B5. The system of any of paragraphs B1-B4, further comprising a crawler system configured to automate the performance of a plurality of laser ultrasound scans of the test specimen by the laser ultrasound device in a plurality of different locations of the test specimen.

B6. The system of paragraph B5, wherein the crawler system is configured to move on a surface of the test specimen.

B7. The system of any of paragraphs B5-B6, wherein the crawler system is configured to move on a test environment surface outside of the test specimen.

B8. The system of any of paragraphs B5-B7, wherein the crawler system is configured to house the laser ultrasound device.

B9. The system of any of paragraphs B5-B8, wherein the crawler system is configured to position the laser ultrasound device relative to the test specimen to perform a laser ultrasound scan on at least a portion of the test specimen.

B10. The system of any of paragraphs B1-B9, wherein the laser ultrasound device comprises an alignment system configured to align and project the laser beam to the desired location on the test specimen.

B11. The system of any of paragraphs B1-1310, wherein the laser ultrasound device comprises a detection system configured to detect the alterations in the detection laser beam as a result of the ultrasonic waves produced in the test specimen.

B12. The system of any of paragraphs B1-B11, wherein the test specimen comprises a sub-scale composite structure, a mid-scale composite structure, and/or a full-scale composite structure.

B13. The system of any of paragraphs B1-B12, wherein at least one of the plurality of NDI sensors comprises an acoustic emission sensor, a PZT transducer, an NDI sensor, an ultrasonic transducer, a bonded PZT sensor, a fiber optic sensor, a stand-off thermography system, a stress gauge, and/or a strain gauge.

B14. The system of any of paragraphs B1-B13, wherein the plurality of NDI sensors are spaced apart on a/the surface of the test specimen.

B15. The system of paragraph B14, wherein respective NDI sensors of the plurality of NDI sensors are positioned in respective areas of the test specimen that are expected to be most likely to experience the highest stresses during use of the test specimen and/or during mechanical testing of the test specimen.

B16. The system of any of paragraphs B1-B15, wherein at least one of the plurality of NDI sensors comprises an ultrasonic transducer that produces A-scans, plate waves, and/or surface waves in the test specimen.

B17. The system of any of paragraphs B1-B16, wherein at least one respective NDI sensor of the plurality of NDI sensors comprises a different type of sensor from at least one different respective NDI sensor of the plurality of NDI sensors.

B18. The system of any of paragraphs B1-B17, wherein the test specimen comprises an in-service part.

B19. The system of any of paragraphs B1-B18, wherein at least one of the plurality of NDI sensors comprises an onboard sensor for an/the in-service part.

B20. The system of any of paragraphs B1-B19, wherein at least one of the plurality of NDI sensors is configured to generate interface waves, such as Stoneley waves, that are configured to interrogate bondlines of the test specimen.

B21. The system of any of paragraphs B1-B20, wherein at least one of the plurality of NDI sensors is configured to generate surface waves, such as Rayleigh waves, that are configured to interrogate micro-cracking and/or surface damage to the test specimen.

B22. The system of any of paragraphs B1-B21, wherein at least one of the plurality of NDI sensors is configured to generate lamb waves that are configured to interrogate impact-induced delamination, disbonds, and/or cracks in the test specimen.

B23. The system of any of paragraphs B1-B22, wherein at least one of the plurality of NDI sensors is configured to generate shear vertical waves that are configured to interrogate skewed defects in the test specimen.

C1. Use of the method of any of paragraphs A1-A77 for sub-scale mechanical testing of the test specimen.

C2. Use of the method of any of paragraphs A1-A77 for full-scale mechanical testing of the test specimen.

C3. Use of the method of any of paragraphs A1-A77 for analysis validation of the test specimen.

C4. Use of the method of any of paragraphs A1-A77 for in-service inspection applications.

C5. Use of the system of any of paragraphs B1-B23 to test and/or inspect the test specimen.

C6. Use of the method of any of paragraphs A1-A77 and/or the system of any of paragraphs B1-B23 to compare in-service (assembled) parts with the as-built record taken during original manufacturing process.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the term "and/or" placed between a first entity and a second entity means one of (1) the first entity, (2) the second entity, and (3) the first entity and the second entity. Multiple entries listed with "and/or" should be construed in the same manner, i.e., "one or more" of the entities so conjoined. Other entities optionally may be present other than the entities specifically identified by the "and/or" clause, whether related or unrelated to those entities specifically identified. Thus, as a non-limiting example, a reference to "A and/or B," when used in conjunction with open-ended language such as "comprising," may refer, in one example, to A only (optionally including entities other than B); in another example, to B only (optionally including entities other than A); in yet another example, to both A and B (optionally including other entities). These entities may refer to elements, actions, structures, steps, operations, values, and the like.

The various disclosed elements of systems and steps of methods disclosed herein are not required to all systems and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

The invention claimed is:

1. A method of testing a test specimen, the method comprising:
monitoring the test specimen with a fixed non-destructive inspection (NDI) sensor fixed with respect to the test specimen, wherein the fixed NDI sensor is configured to monitor indications of damage in or on the test specimen, and wherein the fixed NDI sensor is configured to produce fixed sensor data related to the test specimen;

scanning at least a portion of the test specimen using a laser ultrasound device, thereby producing a first laser ultrasound scan of stress effects within the test specimen, wherein the laser ultrasound device is positioned apart from the test specimen;

storing the first laser ultrasound scan;

mechanically testing the test specimen;

performing a plurality of subsequent respective laser ultrasound scans of stress effects within the test specimen during the mechanically testing the test specimen;

storing each subsequent respective laser ultrasound scan of the test specimen;

comparing each subsequent respective laser ultrasound scan of the test specimen with a previous respective laser ultrasound scan of the test specimen; and integrating scan data from the first laser ultrasound scan with the fixed sensor data from the fixed NDI sensor.

2. The method according to claim 1, wherein the scanning the at least the portion of the test specimen to produce the first laser ultrasound scan comprises scanning substantially an entirety of the test specimen.

3. The method according to claim 1, wherein the integrating scan data and fixed sensor data comprises reconfiguring a mechanical test without stopping the mechanical test, in response to the scan data and the fixed sensor data.

4. The method according to claim 1, wherein the performing the plurality of subsequent respective laser ultrasound scans comprises scanning a plurality of portions of the test specimen corresponding to a plurality of locations of predicted stress sites.

5. The method according to claim 1, further comprising:
determining one or more emergent areas of interest; and
wherein the performing the plurality of subsequent respective laser ultrasound scans comprises scanning a portion of the test specimen corresponding to a respective emergent area of interest.

6. The method according to claim 5, further comprising performing a high-resolution laser ultrasound scan of the one or more emergent areas of interest, wherein the high-resolution laser ultrasound scan comprises a high-density full-waveform scan.

7. The method according to claim 6, wherein the scanning the at least the portion of the test specimen to produce the first laser ultrasound scan is performed at a first resolution, wherein the performing the high-resolution laser ultrasound scan of the one or more emergent areas of interest is performed at a second resolution, and wherein the second resolution is greater than the first resolution.

8. The method according to claim 5, wherein the determining one or more emergent areas of interest comprises one or more of the comparing each subsequent respective laser ultrasound scan of the test specimen with the previous respective laser ultrasound scan, and triangulating based on data from one or more fixed NDI sensors.

9. The method according to claim 5, wherein the scanning at least the portion of the test specimen and the performing the plurality of subsequent respective laser ultrasound scans include detecting damage initiation and growth throughout a depth of the test specimen.

10. The method according to claim 1, further comprising mapping a response of the test specimen to being mechanically tested.

11. The method according to claim 1, wherein the scanning at least the portion of the test specimen using the laser ultrasound device comprises generating and directing a pulsed laser beam towards the test specimen, thereby creating an area of local heating expansion within the test specimen and generating resulting ultrasonic waves.

12. The method according to claim 11, further comprising:
emitting a detection laser beam from the laser ultrasound device;
projecting the detection laser beam onto a surface of the test specimen; and
detecting an alteration of the detection laser beam as a result of the ultrasonic waves.

13. The method according to claim 1, wherein the performing the plurality of subsequent respective laser ultrasound scans and the comparing each subsequent respective laser ultrasound scan are performed in real-time.

14. The method according to claim 1, further comprising:
mounting the fixed NDI sensor;
wherein the mounting the fixed NDI sensor comprises mounting a plurality of fixed NDI sensors spaced apart on a surface of the test specimen, wherein the plurality of fixed NDI sensors are positioned in respective areas of the test specimen that are expected to be most likely to experience the highest stresses during mechanical testing of the test specimen.

15. The method according to claim 1, wherein the fixed NDI sensor comprises an ultrasonic transducer that produces one or more of A-scans, plate waves, and surface waves in the test specimen, and wherein the method further comprises:
generating an acoustical wave using the fixed NDI sensor to internally interrogate the test specimen; and
controlling a frequency of the acoustical wave.

16. The method according to claim 1, further comprising:
monitoring the fixed sensor data during the mechanically testing the test specimen;
comparing the fixed sensor data to expected signal values; and
identifying locations of the test specimen corresponding to fixed sensor data from a respective fixed NDI sensor that differs from the expected signal values.

17. The method according to claim 16, further comprising monitoring one or more stand-off wide-field sensors for any signal differing from expectations or in areas of the test specimen not predicted to be stress sites.

18. The method according to claim 1, further comprising measuring, identifying, and tracking damage indications in the test specimen in real-time.

19. A system for testing a test specimen, the system comprising:
the test specimen;
a laser ultrasound device located apart from the test specimen, wherein the laser ultrasound device is configured to generate and direct a laser beam at the test specimen, thereby producing a plurality of ultrasonic waves within the test specimen, wherein the laser ultrasound device is further configured to produce a detection laser beam and measure an alteration in the detection laser beam as a result of the plurality of ultrasonic waves, and wherein the laser ultrasound device is further configured to scan at least a portion of the test specimen and produce a respective laser ultrasound scan of stress effects within the test specimen periodically during mechanical testing of the test specimen;
a plurality of fixed NDI sensors fixed to the test specimen and spaced apart on a surface of the test specimen, wherein each respective fixed NDI sensor is configured to produce fixed sensor data related to a respective location of the test specimen corresponding to the respective fixed NDI sensor; and a processor configured to integrate data from the plurality of fixed NDI sensors and from the respective laser ultrasound scans produced by the laser ultrasound device to monitor or inspect the test specimen during mechanical testing of the test specimen.

20. The system according to claim 19, further comprising a mechanical stress fixture configured to mechanically test the test specimen, wherein at least one of the plurality of fixed NDI sensors comprises at least one of an acoustic emission sensor, a PZT transducer, an NDI sensor, an ultrasonic transducer, a bonded PZT sensor, a fiber optic sensor, a stand-off thermography system, a stress gauge, and a strain gauge, and wherein at least one of the plurality of fixed NDI sensors comprises an ultrasonic transducer that produces at least one of A-scans, plate waves, and surface waves in the test specimen.

* * * * *